United States Patent [19]

Unal et al.

[11] Patent Number: 5,734,165
[45] Date of Patent: Mar. 31, 1998

[54] MICROSTRUCTURED INFRARED ABSORPTION PHOTOMETER

[75] Inventors: Nezih Unal, Dortmund; Helge Pannhoff, Hamburg; Dierk Landwehr, Dulmen; Lothar E. Durselen, Hilden, all of Germany

[73] Assignees: Microparts Gesellschaft Fuer Mikrostrukturtechnik mbH, Dortmund; Huels Aktiengesellschaft, Marl, both of Germany

[21] Appl. No.: 692,219

[22] Filed: Aug. 7, 1996

[30] Foreign Application Priority Data

Aug. 7, 1995 [DE] Germany .................. 195 28 919.6

[51] Int. Cl.[6] .................. G01N 21/17; G01N 21/35
[52] U.S. Cl. .................. 250/338.1; 250/339.12; 250/339.13; 250/343
[58] Field of Search .................. 250/338.1, 339.1, 250/339.2, 339.07, 339.11, 339.12, 343, 370.12, 339.13

[56] References Cited

U.S. PATENT DOCUMENTS

| | | |
|---|---|---|
| 4,245,155 | 1/1981 | Witting. |
| 4,681,443 | 7/1987 | Bach et al. . |
| 4,784,935 | 11/1988 | Ehrfeld et al. . |
| 5,026,160 | 6/1991 | Dorain et al. .................. 356/328 |
| 5,041,723 | 8/1991 | Ishida et al. .................. 250/339.13 X |
| 5,281,825 | 1/1994 | Berndt et al. . |
| 5,303,026 | 4/1994 | Strobl et al. .................. 356/318 |
| 5,550,375 | 8/1996 | Peters et al. .................. 250/343 |

OTHER PUBLICATIONS

Richardson et al., "A Novel Infrared Spectrometer Using a Linear Array Detector," Applied Spectroscopy, vol. 44, No. 5 1990, pp. 822–825.

*Primary Examiner*—Edward J. Glick
*Attorney, Agent, or Firm*—Oblon, Spivak, McClelland, Maier & Neustadt, P.C.

[57] ABSTRACT

Gases can be selectively detected by utilization of an infrared (IR) absorption photometer via their specific absorption in the IR range. Known instruments are generally rather expensive, are of considerable size, require careful treatment and as a rule can be operated by skilled personnel only. The microstructured IR absorption photometer of the present invention is developed for (quasi-) continuously controlling a gaseous stream, the photometer being a single-piece shaped part manufactured as a microstructured body. The photometer is compact and robust, suitable for portable instruments and can be manufactured at low cost and in large numbers. The photometer can be made of metal and can be used even at an increased temperature. A flashlight lamp serves as an IR radiation source and a lead selenide receiver as an IR radiation receiver. The pulse repetition frequency of the flashlight lamp is from 0.01 Hz to 10 Hz. The pulse interval preferably amounts to more than a thousand times the pulse duration. By using the inventive photometer the safety of systems in which flammable, toxic, or other gases are contained or may occur can be considerably increased in an economic manner.

8 Claims, 1 Drawing Sheet

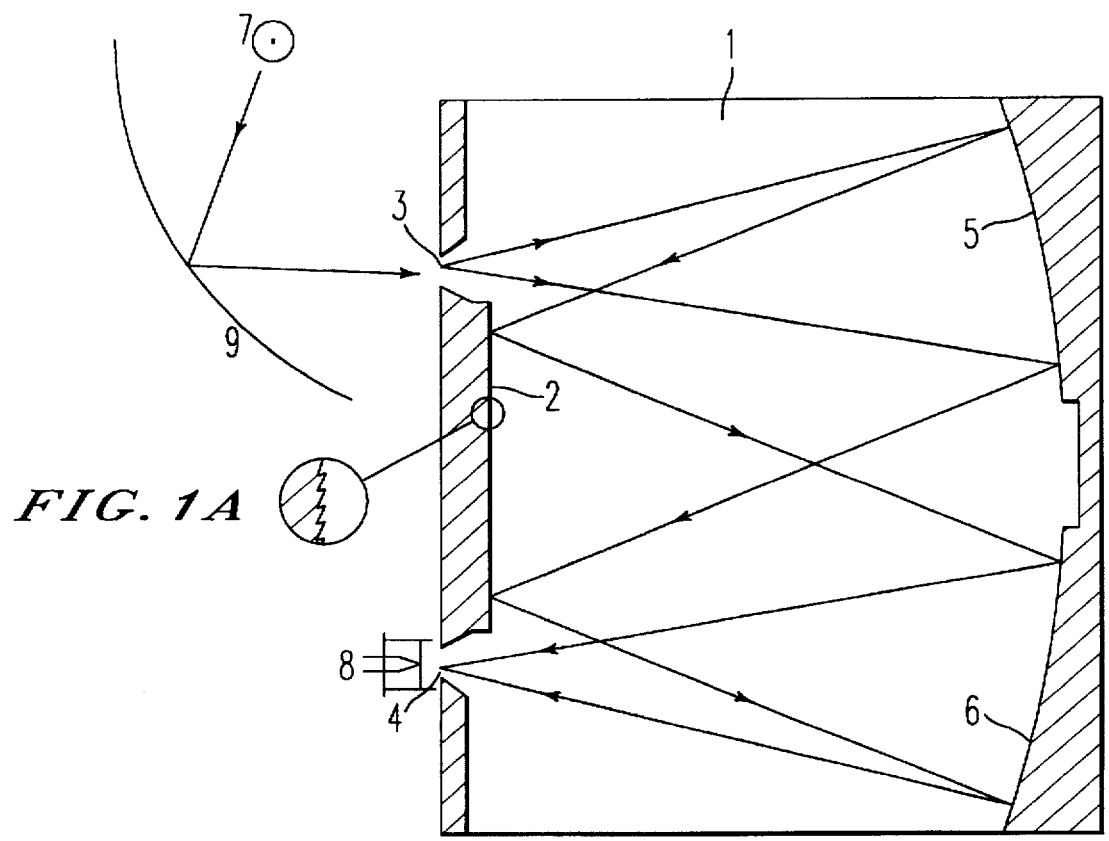
*FIG. 1A*
*FIG. 1*
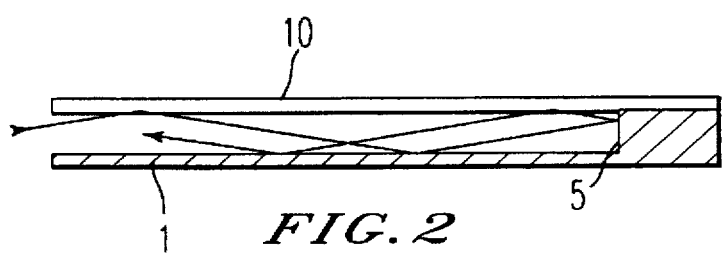
*FIG. 2*

MICROSTRUCTURED INFRARED ABSORPTION PHOTOMETER

BACKGROUND OF THE INVENTION

Field of the Invention

The present invention relates to a microstructured photometer for the infrared (IR) spectral range for detection of absorbing material or mixtures thereof, e.g. within fluids. Furthermore, the invention relates to a procedure for measuring absorption (extinction) by means of this photometer.

DISCUSSION OF THE BACKGROUND

Absorption photometry can be carried out using known spectral photometers, in which the multi-frequency radiation is dispersed by means of a grating. These instruments can be used to address a very wide range of complex problems and to obtain accurate results. However, the known instruments are of considerable size, are generally used only in a fixed position and are comparatively expensive. Tuning through a broader spectral range as a rule requires long measuring times. The instruments demand careful treatment and handling and as a rule can be operated only by skilled personnel.

In addition to spectral photometers also filter photometers are known, in which the spectral range for measuring the absorption is achieved with the aid of optical filters, e.g. interference filters.

Measuring the absorption of a specific material as a rule only requires a narrow spectral range. If a plurality of materials are to be analyzed absorption has to be measured in several spectral ranges. A reference wavelength can be used for eliminating external effects.

DE -44 43 814.2 describes an IR spectrometric sensor for gases, which consists of a microstructured shaped part containing a mirror grating, a connection for injecting multi-frequency IR radiation as well as a connection for extracting single-frequency IR radiation.

The known photometers contain a radiation source and at least one radiation receiver, which is impinged by a beam being attenuated by the gas to be detected. The radiation receiver may be impinged at short intervals by dispersed radiation of different wavelengths. This can be achieved preferably by rotating the monochromatic illuminator. During the operation condition of the photometer the radiation source is permanently switched on. The radiation receiver is either permanently exposed to the dispersed radiation or the path of rays is interrupted by means of a chopper. The chopper may work mechanically.

In the IR range thermal sources or semiconductor diodes can be used. Thermal radiators having a sufficient radiant flux within the IR range emit very much heat into the surrounding. In time, this results in heating up surrounding components which then emit IR radiation too. Thus the output signal is disturbed and masked. This disturbance becomes apparent especially in a compactly built microstructured IR photometer. After sufficient heating up of the instrument the slit used for injecting IR radiation no longer has clear outlines. Thus the resolution of the photometer is diminished or lost at all. Furthermore, the known thermal radiators having sufficient power are slowly-acting and unsuitable for intermittent operation.

SUMMARY OF THE INVENTION

An object of the present invention is therefore to provide for an IR radiation source suitable for a microstructured IR photometer by which the instrument is heated up as little as possible.

This object is achieved according to the invention by a microstructured IR absorption photometer which comprises a single-piece shaped part manufactured as a microstructured body, which comprises a base plate, a mirror grating for dispersing the IR radiation, a connection for injecting multi-frequency IR radiation, and at least one connection for extracting single-frequency IR radiation; a free space between the mirror grating and the connections for the IR radiation; a cover plate above the free space, which cover plate is joined to the shaped part; an IR radiation source; and at least one radiation receiver characterized in that the microstructured absorption photometer comprises a flashlight lamp as an IR radiation source and the IR radiation receiver has a response time which is shorter than the pulse duration of the flashlight lamp.

Commercial gas discharge lamps are suitable flashlight lamps, e.g. discharge lamps filled with xenon gas. The smallest models are tubular lamps some centimeters long and a few millimeters in diameter. Miniaturized models may be even smaller. The pulse duration of the flashlight lamp may be some microseconds during which light of considerable intensity is emitted.

Suitable radiation receivers include e.g. such IR radiation receivers the response time of which is from $0.5 \cdot 10^{-6}$ seconds to 1 second, e.g. lead selenide receivers.

The single-piece shaped part manufactured as microstructure may be made of plastic (e.g. poly(methyl methacrylate), polysulphone, polycarbonate) or of metal (e.g. nickel, nickel-cobalt, gold, copper).

By means of the microstructured IR absorption photometer according to the invention the absorption of a fluid is measured using a pulse repetition frequency from 0.01 Hz to 10 Hz and a pulse duration from $10^{-6}$ seconds to 1 second. The pulse interval preferably amounts to more than a thousand times the pulse duration.

The microstructured IR absorption photometer may contain more than one exit slit and more than one IR radiation receiver mounted behind each slit. Thus it is possible to measure the absorption of the fluid to be tested at several neighboring wavelengths. A further wavelength at which no absorption occurs may be used as a reference wavelength.

The microstructured IR absorption photometer according to the invention is used for quantitative analysis of gases and gas mixtures, e.g. gaseous hydrocarbons (methane, ethane, propane, butane, and others) or of carbon dioxide, carbon monoxide, nitrogen oxide, water vapor, ammonia, and others.

The material to be tested is located in the preferably open space between the flashlight lamp and the entrance slit. Through this space, e.g. the gas to be tested may flow by convection, or gaseous components may reach this space by diffusion.

The microstructured IR absorption photometer according to the invention has the following advantages:

(a) Due to the short pulse duration and the low pulse repetition frequency the heat dissipation is low. Temperature of the IR photometer is only a little bit or not at all higher than the temperature of the environment;

(b) If fluids are tested the composition of which varies only within long periods of time (within minutes or hours) slowly or only insignificantly a low pulse repetition frequency is sufficient to detect such variations reliably. The microstructured IR absorption photometer is most suitable for low pulse repetition frequencies;

(c) The high intensity of the flashlight within the IR range allows the use of inexpensive detectors having moderate sensitivity to detect single-frequency IR radiation;

(d) The flashlight lamp is mechanically less sensitive than a thermal radiation source having a spiral-wound glow filament;

(e) The microstructured IR absorption photometer as a whole is insensitive to vibration and is very suitable for portable instruments;

(f) The service life of the flashlight lamp operated at low pulse repetition frequencies amounts to many years and is appreciably greater than the service life of thermal radiation sources. Therefore, the microstructured IR absorption photometer requires only a very small expenditure for maintenance;

(g) Even at low pulse repetition frequencies the fluid to be tested can be monitored quasi-continuously as long as the composition of the fluid varies only gradually.

Accordingly, the present invention provides for a microstructured infrared (IR) absorption photometer which comprises a single-piece shaped part manufactured as a microstructured body. The shaped part comprises a base plate, a mirror grating for dispersing IR radiation, a connection for injecting multi-frequency IR radiation, at least one connection for extracting single-frequency IR radiation, a free space disposed between the mirror grating and the connections for injecting and extracting IR radiation respectively, and a cover plate above the free space.

The microstructured IR absorption photometer further comprises an IR radiation source, and at least one IR radiation receiver.

The IR radiation source is a flashlight lamp, and the IR radiation receiver has a response time which is shorter than a pulse duration of the flashlight lamp.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a view of the microstructured IR absorption photometer of the present invention; and FIG. 1a is an enlarged view of a feature of FIG. 1.

FIG. 2 is a longitudinal section through the microstructured IR absorption photometer of the present invention.

DESCRIPTION OF THE PREFERRED EMBODIMENTS

Referring now to the drawings, wherein like reference numerals designate identical or corresponding parts throughout the several views, FIG. 1 illustrates a view of the microstructured IR absorption photometer as seen from an open side of a free space. Arranged on the base plate (1) there are a planar mirror grating (2) also seen in FIG. 1a, a slit (3) for injecting multifrequency IR radiation, and a slit (4) for extracting single-frequency IR radiation. Concave mirrors (5) and (6) are situated opposite the mirror grating (2). Between the mirror grating (2) and the concave mirrors (5) and (6) there is the free space. The longitudinal sides of the free space may be open or closed. A flashlight lamp (7) as an IR radiation source is arranged on the outside of the injection slit (3) and an IR radiation receiver (8) is arranged on the outside of the extraction slit (4). The radiation of the flashlight lamp (7) is focused on the injection slit (3) by means of a concave mirror (9). The parts shown hatched in FIG. 1 project above the base plate (1). The base plate (1) together with the elements (2) and (6) fixedly arranged thereon form the microstructured single-piece shaped part.

By means of the two concave mirrors (5) and (6), the IR beam is reflected within the free space in order to extend its path.

The material to be tested is located in the space between the flashlight lamp (7), concave mirror (9) and entrance slit (3). This space is open and a gas, e.g., can flow through this space.

FIG. 2 illustrates a longitudinal section through the inventive microstructured IR absorption photometer. The free space is covered by a cover plate (10). The radiation coming from the IR radiation source undergoes multiple reflection on the walls of the free space.

Example

Microstructured IR absorption photometer for flammable gases

Flammable hydrocarbons such as methane, ethane, propane and butane, absorb IR radiation in the range of 3.38 µm (2960 cm$^{-1}$). The detection of propane in the air makes use of a microstructured IR absorption photometer according to the invention.

The microstructured IR absorption photometer according to FIG. 1 is approximately 25 mm long and approximately 20 mm wide. The free space has a height of approximately 500 µm. The inside of the microstructured shaped part fabricated by means of the LIGA technique and made of poly(methyl methacrylate) and the inside of the cover plate made of poly(methyl methacrylate) are gold-plated, as is the mirror grating. The mirror grating has 200 lines/mm. The blaze angle is matched to the maximum reflection of the mirror grating in the range 3.4 µm (2940 cm$^{-1}$) in the first order of diffraction.

The IR photometer entrance slit (3), which has a width of approximately 0.4 mm is illuminated with a flashlight lamp, e.g. the xenon gas filled flash tube BGA 1020 TAR 3 (manufactured by Heimann). This flash tube is 34 mm long and has a diameter of 3.15 mm. The tube is made of hard glass. The bias voltage amounts to 320 V and the ignition voltage to 11 kV. The mean energy amounts to about 2 Ws per pulse, and the pulse duration is about 10 µs. This flashlight lamp has a high radiant intensity in the range around 3.4 µm (2940 cm$^{-1}$). The light of the flashlight lamp (7) is focused on the entrance slit (3) by means of the concave mirror (9) which is mounted about 2 cm in front of the entrance slit.

The radiation reflected by mirror grating (2) is directed onto the exit slit (4) having a width of approximately 0.4 mm. The slit (4) is situated at the position at which the wavelength 3.4 µm (2940 cm$^{-1}$) appears. Behind the exit slit (4) a lead selenide radiation receiver is arranged, the response time of which is about 1.5 µs; this is less than the pulse duration of the flashlight.

The space between the concave mirror (9) and the entrance slit (3) serves as a gas cuvette without side walls. The gas is flowing by convection through this space with a throughput of about 100 cm$^3$ per minute. The gas essentially consists of air and may at times contain propane.

As soon as propane is present in the gas to be tested, the intensity received by the radiation receiver at 3.38 µm (2960 cm$^{-1}$) diminishes in accordance with the extinction law as the concentration of propane increases.

This IR absorption photometer can be used to detect propane percentages in air, which amount to approximately 10% of the propane concentration of the ignitable mixture of propane and air, i.e. approximately 0.2% propane in air.

This makes it possible to detect e.g. leaks in gas-operated systems. The lower explosion limit of a propane-air mixture is about 1.8% propane.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A microstructured infrared (IR) absorption photometer comprising:

a single-piece shaped part manufactured as a microstructured body, said shaped part comprising a base plate, a mirror grating for dispersing IR radiation, a connection for injecting multi-frequency IR radiation, at least one connection for extracting single-frequency IR radiation, a free space disposed between the mirror grating and the connections for injecting and extracting IR radiation respectively, and a cover plate above the free space;

an IR radiation source; and at least one IR radiation receiver;

wherein:
      the IR radiation source is a gas discharge lamp having a pulse duration from 1 microsecond to 1 second, and the IR radiation receiver is a semiconductor receiver having a response time which is shorter than the pulse duration of said gas discharge lamp.

2. A microstructured IR absorption photometer according to claim 1, wherein:

the gas discharge lamp is a xenon gas filled flashlight lamp; and the IR radiation receiver is a lead selenide radiation receiver.

3. A microstructured IR absorption photometer according to claim 1, wherein:

said microstructured single-piece shaped part is composed of plastic.

4. A microstructured IR absorption photometer according to claim 1, wherein:

said microstructured single-piece shaped part is composed of metal.

5. A method for measuring an absorption of fluids by means of a microstructured infrared IR absorption photometer, the microstructured infrared photometer comprising:

a single-piece shaped part manufactured as a microstructured body, said shaped part comprising a base plate, a mirror gating for dispersing IR radiation, a connection for injecting multi-frequency IR radiation, at least one connection for extracting single-frequency IR radiation, a free space disposed between the mirror grating and the connections for injecting and extracting IR radiation respectively, and a cover plate above the free space;

an IR radiation source; and at least one IR radiation receiver;

wherein:
      the IR radiation source is a gas discharge lamp having a pulse duration from 1 microsecond to 1 second, and the IR radiation receiver is a semiconductor receiver having a response time which is shorter than the pulse duration of said gas discharge lamp; the method comprising the steps of:
         selecting a pulse repetition frequency of the gas discharge lamp from 0.01 Hz to 10 Hz; and
         selecting a response time of said IR radiation receiver from 0.5 microseconds to 1 second.

6. A method according to claim 5, wherein a pulse interval is selected which is more than a thousand times greater than the pulse duration.

7. An application of a microstructured infrared IR absorption photometer for quantitative analysis of gases or gas mixtures, the microstructured infrared IR photometer comprising:

a single-piece shaped part manufactured as a microstructured body, said shaped part comprising a base plate, a mirror grating for dispersing IR radiation, a connection for injecting multi-frequency IR radiation, at least one connection for extracting single-frequency IR radiation, a free space disposed between the mirror grating and the connections for injecting and extracting IR radiation respectively, and a cover plate above the free space;

an IR radiation source; and at least one IR radiation receiver;

wherein:
      the IR radiation source is a gas discharge lamp having a pulse duration from 1 micro-second to 1 second, and the IR radiation receiver is a semiconductor receiver having a response time which is shorter than the pulse duration of said gas discharge lamp.

8. An application according to claim 7, wherein said gases or gas mixtures are gaseous hydrocarbons or carbon dioxide, carbon monoxide, nitrogen oxide, water vapor or ammonia.

* * * * *